US008663255B2

(12) United States Patent
Torain et al.

(10) Patent No.: US 8,663,255 B2
(45) Date of Patent: Mar. 4, 2014

(54) GASTRIC BAND WITH OVERMOLD (75) Inventors: Stephen M. Torain, Cincinnati, OH (US); Harry E. Payne, Loveland, OH (US); Jeffrey P. Wiley, Milford, OH (US); Lauren S. Weaner, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 69 days.

(21) Appl. No.: 13/205,853

(22) Filed: Aug. 9, 2011

(65) Prior Publication Data
US 2013/0041389 A1 Feb. 14, 2013

(51) Int. Cl.
*A61B 17/12* (2006.01)

(52) U.S. Cl.
USPC ............................................. 606/151; 600/37

(58) Field of Classification Search
CPC ..... A61F 5/005; A61F 5/0053; A61F 5/0056; A61F 5/0063; A61F 5/0066
USPC ..................... 600/37; 606/151–157, 201–203
See application file for complete search history.

(56) References Cited

U.S. PATENT DOCUMENTS

| 4,997,438 | A | * | 3/1991 | Nipper ........................ 606/201 |
| 6,067,991 | A | | 5/2000 | Forsell |
| 6,461,292 | B1 | | 10/2002 | Forsell |
| 6,470,892 | B1 | | 10/2002 | Forsell |
| 7,364,542 | B2 | * | 4/2008 | Jambor et al. ................. 600/37 |
| 7,367,937 | B2 | | 5/2008 | Jambor et al. |
| 7,416,528 | B2 | | 8/2008 | Crawford et al. |
| 7,442,165 | B2 | | 10/2008 | Forsell |
| 7,621,863 | B2 | | 11/2009 | Forsell |
| 7,699,770 | B2 | | 4/2010 | Hassler, Jr. et al. |
| 7,775,215 | B2 | | 8/2010 | Hassler, Jr. et al. |
| 7,850,660 | B2 | | 12/2010 | Uth et al. |
| 8,016,745 | B2 | | 9/2011 | Hassler, Jr. et al. |
| 2006/0178564 | A1 | | 8/2006 | Jones et al. |
| 2007/0185518 | A1 | | 8/2007 | Hassler, Jr. |
| 2011/0144420 | A1 | | 6/2011 | Woodruff et al. |

FOREIGN PATENT DOCUMENTS

| EP | 1 520 563 | 4/2005 |
| EP | 1 864 625 | 12/2007 |

OTHER PUBLICATIONS

International Search Report dated Mar. 10, 2011 for Application No. PCT/US2010/059129.

* cited by examiner

*Primary Examiner* — Julian W Woo
*Assistant Examiner* — Shaun L David
(74) *Attorney, Agent, or Firm* — Frost Brown Todd LLC (57) ABSTRACT

A gastric band comprises a bladder having an opening, an insertable component to fluidly seal the opening, and a strap that may be overmolded onto the bladder. The insertable component may be a grommet or a plug. Additionally, the insertable component may be coupled to a support member via a living hinge. In another configuration, the insertable component comprises a grommet and a suture loop at least partially formed within the grommet. A band may be provided instead of the strap, with the band having a grommet aperture formed through a deck such that the grommet may be inserted into the opening of the bladder. An overmolded shell having a latching member may be overmolded onto the deck to secure the grommet and a portion of the suture loop therein. The gastric band may further be coupled to a flexible conduit and an injection port.

4 Claims, 11 Drawing Sheets

GASTRIC BAND WITH OVERMOLD

BACKGROUND

Implantable medical devices may be implanted in a patient to perform a therapeutic function for that patient. Non-limiting examples of such devices include pace makers, access ports (such as vascular access ports, infusion ports, and ports used with gastric band systems, etc.) and gastric pacing devices. Such implants may need to be attached, perhaps subcutaneously, in an appropriate place in order to function properly. It may be desirable that the procedure to implant such devices be quick, easy and efficient.

Ports may be placed beneath the skin of a body for injecting fluids into or withdrawing fluids from the body. By way of example, vascular access ports may be used for infusing medication, blood draws, and many other applications. Injection ports may be used for adding or withdrawing fluid in adjustable gastric band systems. These various access ports may include an implantable port housing coupled to a fluid conduit which delivers fluid to or withdraws fluid from a location in the patient's body (e.g., a vein or a gastric band, etc.).

Gastric band systems are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,367,937, entitled "Gastric Band," issued May 6, 2008, the disclosure of which is incorporated by reference herein; U.S. Pat. No. 7,416,528, entitled "Latching Device for Gastric Band," issued Aug. 26, 2008, the disclosure of which is incorporated by reference herein; and in U.S. Pat. No. 6,067,991, entitled "Mechanical Food Intake Restriction Device," issued May 30, 2000, the disclosure of which is incorporated by reference herein.

To the extent that an adjustable gastric band system includes an injection port configured to receive the needle of a syringe assembly in order to add or withdraw fluid to or from the gastric band, those of ordinary skill in the art will appreciate that it may be desirable in some settings to locate both the injection port and, more specifically, the center of the injection port (e.g., when the septum of the injection port is at the center of the injection port). Locating the approximate center of the injection port with some degree of accuracy may facilitate addition or withdrawal of fluid via the injection port to adjust the gastric band system. One example of a system and method for identifying the location of an injection port is disclosed in U.S. Pub. No. 2006/0211914, entitled "System and Method for Determining Implanted Device Positioning and Obtaining Pressure Data" published Sep. 21, 2006, and issued Aug. 17, 2010 as U.S. Pat. No. 7,775,215, the disclosure of which is incorporated by reference herein.

Those of ordinary skill in the art will appreciate that it may be advantageous in certain circumstances to sense pressure, strain, and/or other parameters associated with operation of a gastric band device. In some settings, it may be desirable to obtain data indicative of the pressure of fluid in a gastric band. Various examples of methods and devices for obtaining pressure data and other types of data are disclosed in U.S. Pub. No. 2006/0189888, entitled "Device for Non-Invasive Measurement of Fluid Pressure in an Adjustable Restriction Device," published Aug. 24, 2006, and issued Apr. 20, 2010 as U.S. Pat. No. 7,699,770, the disclosure of which is incorporated by reference herein. Additional examples of methods and devices for obtaining pressure data and other types of data are disclosed in U.S. Pub. No. 2006/0199997, entitled "Monitoring of a Food Intake Restriction Device," published Sep. 7, 2006, and issued Sep. 13, 2011 as U.S. Pat. No. 8,016,745, the disclosure of which is incorporated by reference herein. Such parameter data may be obtained before, during, and/or after adjustment of a gastric band, and may be useful for adjustment, diagnostic, monitoring, or other purposes, and may also be obtained with respect to a mechanically actuated gastric band. In settings where a fluid-filled gastric band is used, pressure data may be used to determine whether the amount of fluid in the gastric band needs to be adjusted; and/or for other purposes.

While a variety of implantable access ports and gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various embodiments of ports having tissue in-growth promoting surfaces and/or features are depicted and described as being part of a gastric band system, the tissue in-growth surfaces and features may be employed with other types of implantable medical ports or other medical devices. Accordingly, the drawings and descriptions should be regarded as illustrative in nature and not restrictive.

I. Exemplary Gastric Band System

FIGS. 1-4 illustrate an exemplary gastric band system (10). As shown, gastric band system (10) comprises an injection port (12), a gastric band (20), and a flexible conduit (or catheter) (18). Injection port (12) of the present example comprises a port housing (14), a needle penetrable septum (16) and a fluid reservoir (not shown in FIGS. 1-4) located beneath septum (16). Catheter (18) (e.g., a flexible and/or resilient polymeric tube) is attached to port housing (14) and is in fluid communication with the fluid reservoir therein. A needle may pierce septum (16) to reach the reservoir and add or withdraw fluid (e.g., saline, etc.), as described in greater detail below.

Figure 1:
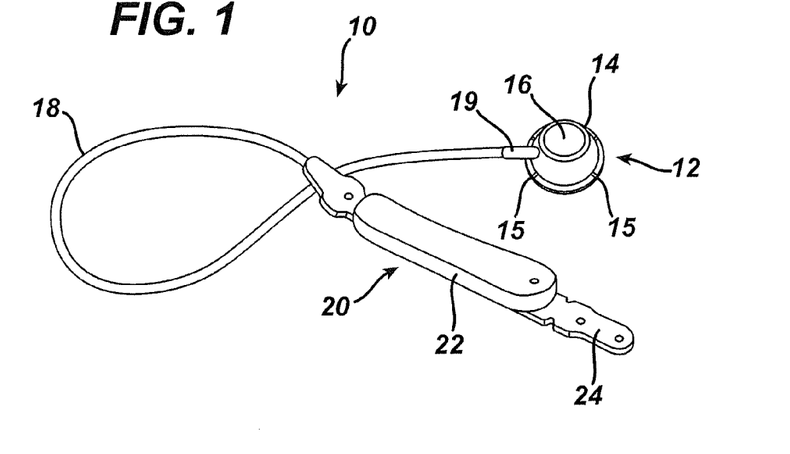
FIG. 1 depicts a perspective view of an implantable portion of an exemplary gastric band system, including an injection port having an integral fluid conduit retention sleeve.

Port housing (14) may comprise a unitary structure (e.g., a one piece housing insert molded about septum (16)). Alternatively, port housing (14) may be assembled from two or more mating components such as a port body which at least partially receives a port base therein. Injection port (12) also includes a retention sleeve (19), which extends about a portion of fluid conduit (18) where conduit (18) is attached to housing (14). Port housing (14) may be formed of titanium, plastic, or any other suitable material or combination of materials. Septum (16) may be formed of silicone or any other suitable material or combination of materials.

Injection port (12) may be subcutaneously secured over a patient's sternum, to the patient's abdominal fascia, or in any other suitable location. By way of example, port (12) may be sutured in place using the suture apertures (15) located about the periphery of port housing (14). In other versions, injection port (12) may be configured and operable in accordance with the teachings of U.S. Pat. No. 7,850,660, entitled "Implantable Medical Device with Simultaneous Attachment Mechanism and Method," issued Dec. 14, 2010, the disclosure of which is incorporated by reference herein. For example, injection port (12) may be configured to include a plurality of fasteners that are selectively deployed from the injection port in order to secure the port in place within a patient, as further described in U.S. Pat. No. 7,850,660. Alternatively, injection port (12) may have any other suitable configuration and/or operability.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). Catheter (18) may be formed of silicone or any other suitable material or combination of materials. In the present example, catheter (18), bladder (22), and injection port (12) form a closed fluid circuit. Accordingly, a needle that is inserted through septum (16) into the underlying reservoir may be used to add fluid to or withdraw fluid from inflatable bladder (22) in order to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
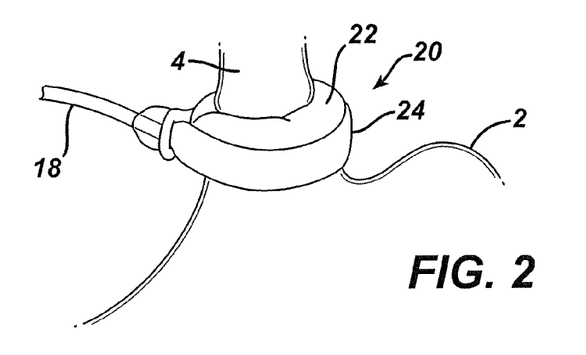
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastro-esophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction, or increased by withdrawing fluid from bladder (22) to reduce the degree of restriction.

Figure 3:
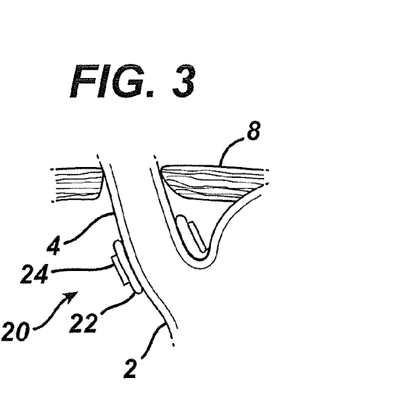
FIG. 3 depicts a cross-sectional view of the gastric band of FIG. 1, showing the band positioned around the gastro-esophageal junction of a patient in a deflated configuration.
Figure 4:
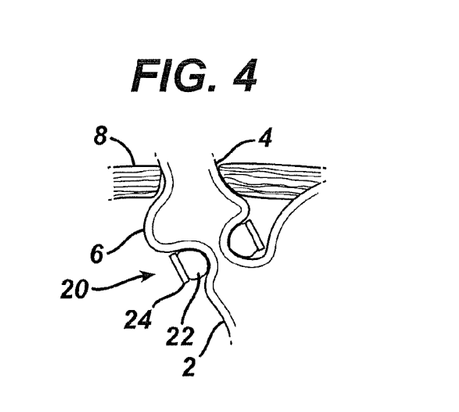
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient.

As mentioned previously, injection port (12) may be subcutaneously secured over a patient's sternum, to the patient's abdominal fascia, or in any other suitable location. In some versions of a gastric band system, catheter (18) may become inadvertently detached from injection port (12), thus allowing fluid to leak from bladder (22) and the fluid reservoir within injection port (12). A retention sleeve (19) includes a plurality of cantilevered, flexible fingers that urge catheter (18) against a tubular stem extending from housing (14), thereby substantially preventing catheter (18) from becoming disconnected from housing (14) after implantation. (The cantilevered fingers and tubular stem are not shown in FIG. 1.) While retention sleeve (19) is shown in FIG. 1 as being an integral part of housing (14), in other versions the retention sleeve is a separate component (or plurality of components) attached to the port housing (14).

II. Exemplary Gastric Band Assembly

In some situations it may be preferable to couple bladder (22) of gastric band (20) to flexible strap (24) without the use of adhesives. For instance, it may be useful to couple bladder (22) of gastric band (20) to a support member to reinforce the outer wall of bladder (22) and/or to provide a surface for overmolding flexible strap (24). Alternatively, bladder (22) may be molded and a plug or grommet may be inserted prior to overmolding flexible strap (24). In yet a further configuration, the grommet may be integrated with the support member to form a unitary piece that may be coupled to bladder (22). In each of these instances, the use of adhesives to couple bladder (22) to flexible strap (24) and/or the support member may be reduced or eliminated. Accordingly, the various configurations for bladder (22) and/or support member will now be described in greater detail.

A. Exemplary Grommet and Bladder

Figure 5:
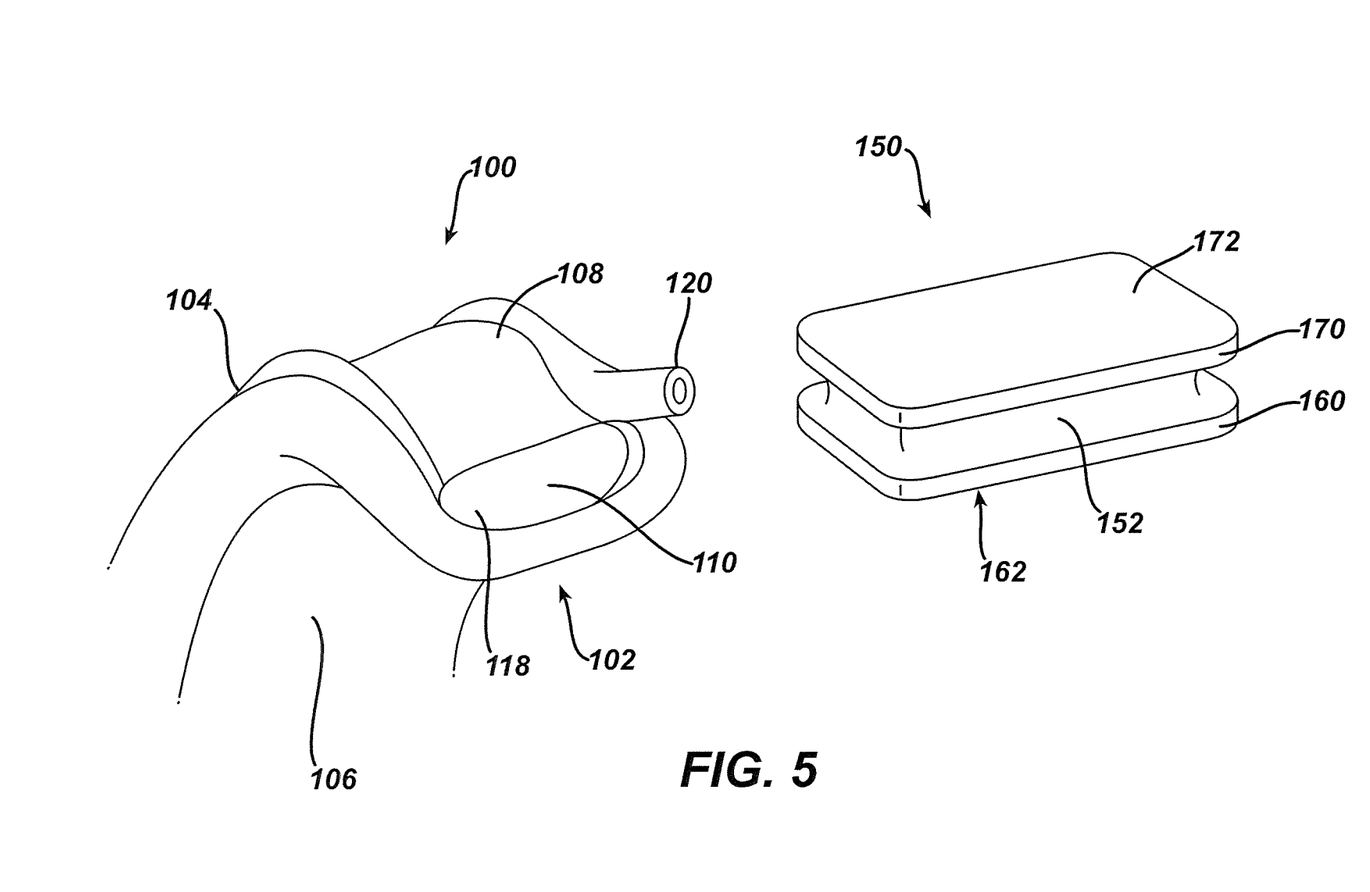
FIG. 5 depicts a perspective view of an exemplary grommet and a partial perspective view of a first end of a gastric band bladder.
Figure 8:
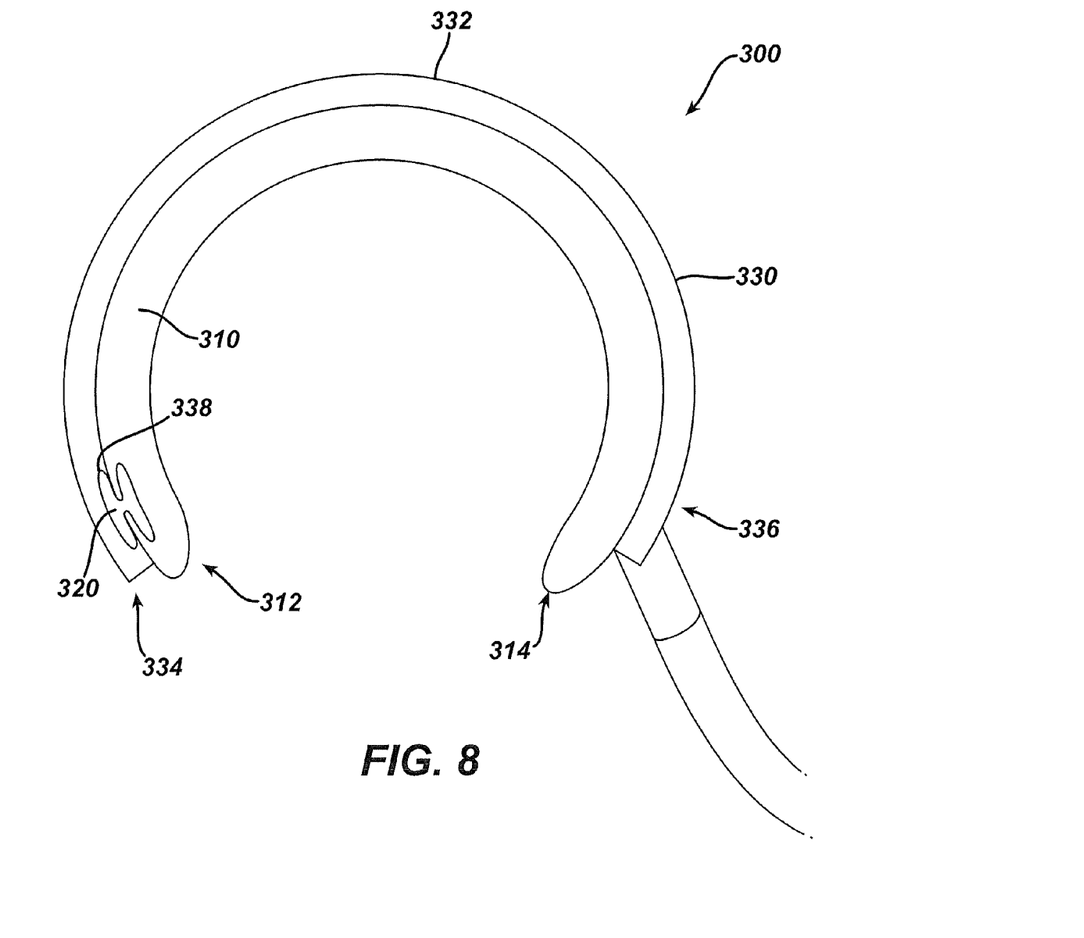
FIG. 8 depicts a side elevation view of an exemplary alternative bladder coupled to a grommet and a support member.

FIG. 5 illustrates an exemplary bladder (100) and grommet (150) for use in a gastric band, such as gastric band (20). Bladder (100) comprises a first end (102), a second end (not shown), an outer surface (104), an inner surface (106), and, optionally, a channel (108). First end (102), second end, outer surface (104), and inner surface (106) collectively define an interior (118) of bladder (100). First end (102) comprises an opening (110) that is in communication with interior (118) and that is configured to receive grommet (150). In some instances, bladder (100) may be formed via injection molding. Such molding may require a mold and a core to define a cavity into which the material for bladder (100) is injected. In the present configuration, the core and mold have a curvature to form a substantially curved bladder (100), as best shown in FIG. 8. To remove the core from the newly formed bladder (100), a portion of the core may protrude from the mold. Such a protrusion may define the size and shape of opening (110). Alternatively, the protrusion may be substantially smaller than a desired opening (110), in which case opening (110) may be formed by removing additional material from bladder (100). Opening (110) of the present example is sized to secure grommet (150) within opening (110) when inner lip (160) of grommet (150) is inserted into opening (110) and outer lip (170) engages outer surface (104) of bladder (100), as will be described in more detail below. In the present example, first end (102) further comprises a bladder inlet (120) that is in fluid communication with interior (118) of bladder (100) Bladder inlet (120) is coupleable to a catheter, such as catheter (18) of FIG. 1, though it should be understood that bladder inlet (120) may be located on the second end of bladder (100), on the outer surface (104), on the inner surface (106), on grommet (150), or be omitted. Bladder (100) of the present example comprises a silicone molded bladder, though other suitable flexible materials may be used for bladder (100). Bladder (100) may further be configured in accordance with at least some of the teachings described herein in reference to bladder (20) or in any other suitable configuration as will be apparent to one of ordinary skill in the art in view of the teachings herein.

Grommet (150) of the present example comprises an inner lip (160), an outer lip (170), an outer surface (172), an inner surface (162), and a central portion (152). Grommet (150) of the present example is a thermoplastic component, though other materials, such as a semi-rigid or rigid rubber, a semi-rigid or rigid silicone, plastics, and/or any other suitable material(s) may be used for grommet (150) as will be apparent to one of ordinary skill in the art in view of the teachings herein. As shown in FIG. 5, inner lip (160) and outer lip (170) extend outwardly from central portion (152) to form two substantially equal sized lips or flanges, though it should be understood that inner lip (160) and/or outer lip (170) may be larger than the other. Furthermore, in the present example, both inner lip (160) and outer lip (170) extend outwardly from central portion (152) in all directions, but it should be understood that inner lip (160) and/or outer lip (170) may extend outwardly from central portion (152) in less than all directions, such as a grommet having two flat, opposing sides and two lipped, opposing sides. Inner lip (160) and outer lip (170) may be configured to form an interference fit with the material surrounding opening (110) when grommet (150) is inserted into opening (110). Such an interference fit may be formed by tapering inner lip (160) and/or outer lip (170) toward the other or, in one alternative, by spacing inner lip (160) and outer lip (170) such that the thickness of the material surrounding opening (110) is greater than the spacing between inner lip (160) and outer lip (170). An adhesive may be applied to grommet (150) to further ensure a fluid-tight seal. Furthermore, while grommet (150) of the present example is depicted as a rectangular shaped member, it should be understood that other geometries for grommet (150) may be used, including cylindraceous grommets, ovular grommets, triangular grommets, or any other suitable configuration as will be apparent to one of ordinary skill in the art in view of the teachings herein.

Figure 6:
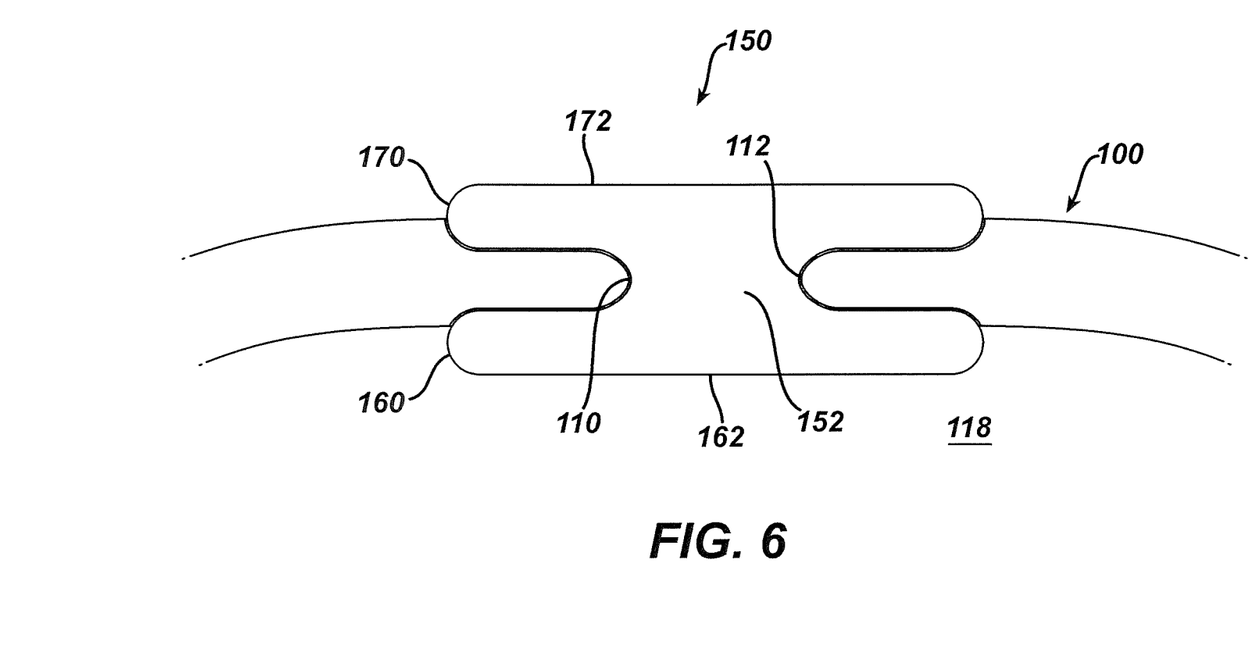
FIG. 6 depicts a partial side cross-sectional view of the grommet inserted into the first end of the bladder of FIG. 5.

FIG. 6 shows grommet (150) inserted into opening (110) of bladder (100).

Central portion (152) of the present example is sized to engage the material defining opening (110) when grommet (150) is inserted into opening (110) of bladder (100). Accordingly, the material defining opening (110) and central portion (152) form a substantially fluid-tight interface such that fluids from within interior (118) cannot leak out opening (110) and/or bodily fluids cannot leak into interior (118). Central portion (152) may further include wiper seal type protrusions to engage an opening surface (112) of opening (110). Such wiper seal protrusions may have a triangular cross-section or a semi-circular cross-section. Furthermore, an adhesive may be applied to central portion (152) prior to inserting grommet (150) into opening (110). In yet another alternative, opening surface (112) of opening (110) may further comprise a bulbous portion encircling a portion, or all, of opening (110) in a similar manner to the end of a balloon. A corresponding bulbous recess may be included on grommet (150) to receive the bulbous portion of opening. The bulbous recess may be sized smaller than the bulbous portion to form a fluid tight interface between grommet (150) and opening surface (112) of opening (110). In another alternative, inner lip (160) and inner surface (162) and/or outer lip (170) and outer surface (172) may be tapered to create a smooth or substantially smooth transition from an interior surface of bladder (100) to inner surface (162) of grommet (150) and/or from outer surface (104) of bladder (100) to outer surface (172) of grommet (150). Still other configurations for grommet (150) and/or bladder (100) will be apparent to one of ordinary skill in the art in view of the teachings herein.

Figure 7:
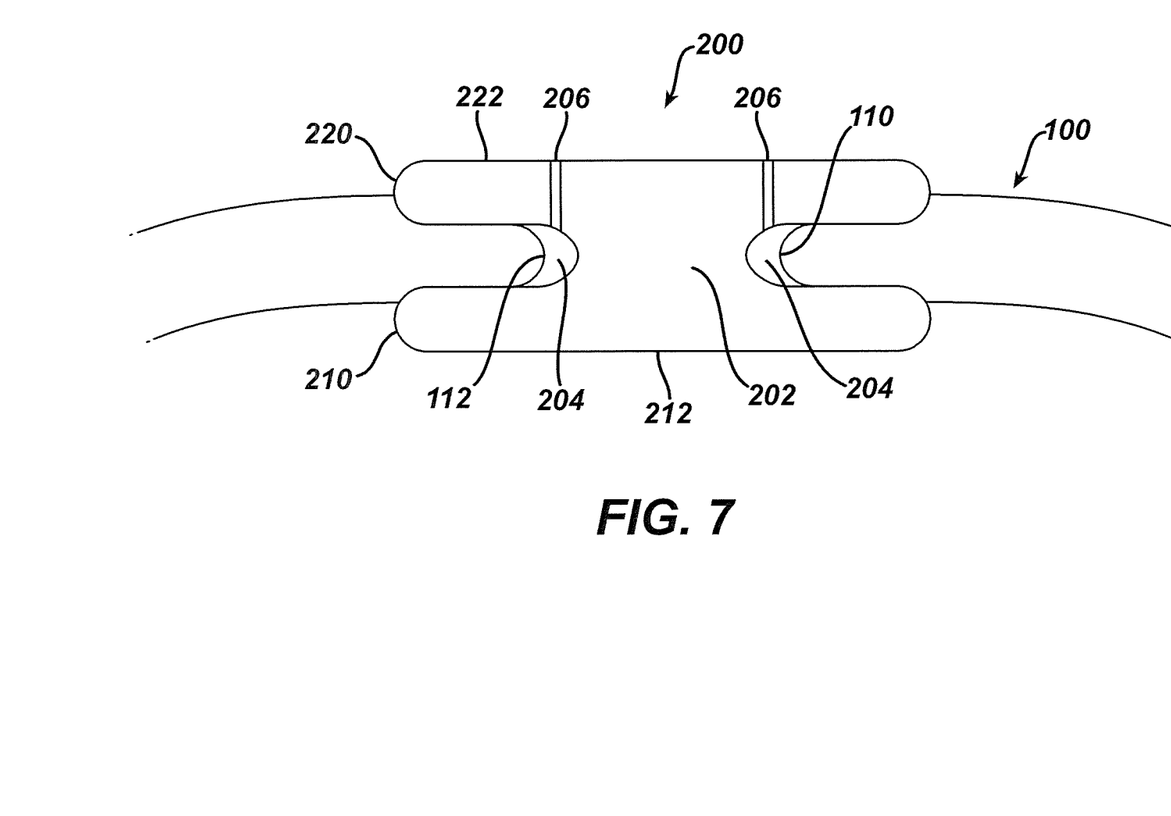
FIG. 7 depicts a partial side cross-sectional view of an exemplary alternative configuration for a grommet inserted into a first end of a bladder.

In yet another configuration shown in FIG. 7, an alternative grommet (200) comprises an inner lip (210), an outer lip (220), an outer surface (222), an inner surface (212), and a central portion (202), and is configured in a substantially similar manner to grommet (150). Grommet (200) is shown inserted into opening (110) of bladder (100). In this configuration, central portion (202) is sized such that opening (110)

does not engage central portion (202). Instead, when grommet (200) is inserted into opening (110), a cavity (204) is defined by central portion (202) and opening surface (112) of opening (110). One or more injection ports (206) are shown extending from outer surface (222) to cavity (204) such that an adhesive may be injected into cavity (204) once grommet (200) is inserted into opening (110). Of course, ports (206) and the adhesive may be omitted and an interference fit between inner lip (210), outer lip (220), and the material surrounding opening (110) may be used in a similar manner to the interface fit described above in reference to grommet (150).

In the configurations shown in FIGS. 6-7, once grommet (150, 200) is inserted into opening (110), strap (24) of FIG. 1 is overmolded onto bladder (100) and grommet (150, 200) to form an assembled gastric band, such as gastric band (20) of FIG. 1. In one configuration, a fluid source may be coupled to bladder inlet (120) to fill bladder (100) with a fluid prior to overmolding strap (24). For instance, air, saline, water, mineral oil, or any other fluid may be injected into bladder (100) to provide a substantially rigid, curved surface onto which strap (24) may be molded. In yet a further configuration, outer surface (172, 222) of grommet (150, 200) may further comprise one or more dimples, divots, channels, or any other suitable feature to further promote adhesion of the overmolded strap (24) to grommet (150, 200). In the foregoing examples, strap (24) comprises a silicone component, though other suitable materials for strap (24) will be apparent to one of ordinary skill in the art in view of the teachings herein.

B. Exemplary Support Member

In some situations, it may be useful to include a rigid or semi-rigid piece to assist in stabilizing bladder (22) in a desired shape while strap (24) is overmolded onto bladder (22). In such instances, not only may a support member provide this stabilization, but the support member may provide further reinforcement to the outer surface of bladder (22) when bladder (22) is filled with fluid.

FIG. 8 depicts an exemplary alternative configuration for a gastric band (300) comprising a bladder (310), a grommet (320), a strap (not shown), and a support member (330). The strap has been omitted to show support member (330) more fully. In this configuration, bladder (310) may be configured in a substantially similar manner to bladder (100) of FIGS. 5-7. Bladder (310) of the present example comprises a first end (312), a second end (314), and a channel (not shown) that is substantially similar to channel (108) shown in FIG. 5. Grommet (320) may be configured in accordance with at least some of the teachings of grommet (150) of FIG. 5-6 or grommet (200) of FIG. 7. Support member (330) comprises a body portion (332), having a first end (334) and a second end (336), and a grommet receiving cavity (338) formed at first end (334). Body portion (332) is a curved member extending along the channel formed in the outer surface of bladder (310) such that first end (334) of body portion (332) corresponds to first end (312) of bladder (310) and second end (336) of body portion (332) corresponds to second end (314) of bladder (310). Support member (330) of the present example is a thermoplastic component, though it should be understood that substantially rigid elastomeric components, metallic components, or other suitable rigid or semi-rigid materials may be used for support member (330).

In the present configuration, support member (330) is overmolded onto bladder (310) and grommet (320), thereby forming grommet receiving cavity (338) and containing a portion of grommet (320) therein. Alternatively, support member (330) may be pre-formed to have grommet receiving cavity (338). In this configuration, support member (330) is coupled to grommet (320) and bladder (310) by inserting a portion of grommet (320), such as outer lips (170, 220) described above, into grommet receiving cavity (338). A reinforcing band (not shown) may also be inserted into bladder (310) or may extend along the channel formed in bladder (310), such as the reinforcing belt described in U.S. Pat. No. 7,367,937, entitled "Gastric Band," issued May 6, 2008. When support member (330) is overmolded or coupled to grommet (320), support member (330) substantially covers the reinforcing band. Alternatively, the reinforcing band may be molded over support member (330) after support member (330) is coupled to grommet (320) or overmolded onto bladder (310). Once support member (330) and the optional reinforcing band are attached, a strap, such as strap (24) of FIG. 1, is overmolded onto support member (330). Support member (330) may further maintain bladder (310) in the desired curved shape during this overmolding process. Support member (330) may also provide a mounting surface for the strap to be molded onto. As can be appreciated by one of ordinary skill in the art in view of the teachings herein, support member (330), the strap, and, optionally, the reinforcing band substantially constrain the outer surface of bladder (310). When fluid is injected into bladder (310) and bladder (310) swells about stomach (2), the restraint provided by support member (330), the strap, and/or the reinforcing band may urge bladder (310) to compress stomach (2) as opposed to expanding support member (330), the strap, and/or the reinforcing band. Other suitable configurations and features for support member (330), grommet (320), and bladder (310) will be apparent to those of ordinary skill in the art in view of the teachings herein.

Figure 9:
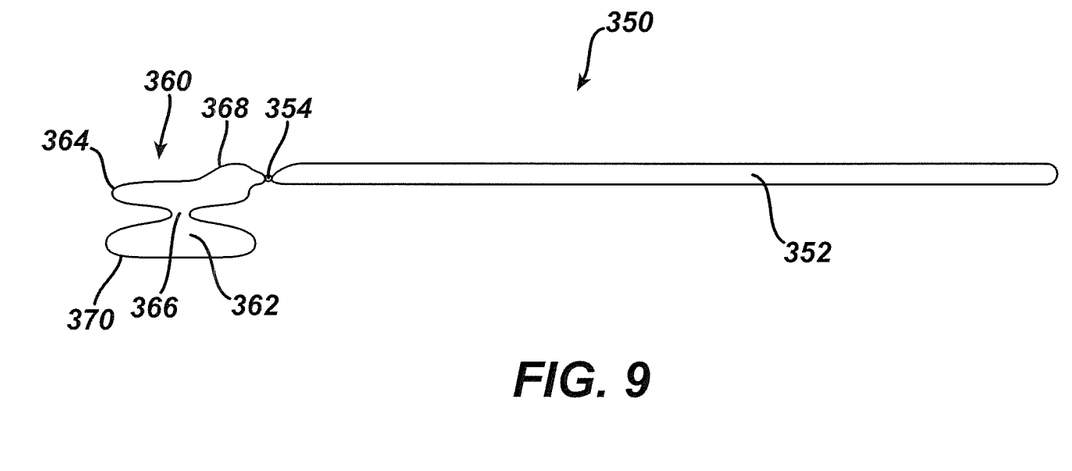
FIG. 9 depicts a side elevation view of yet another exemplary alternative grommet coupled to a support member by a living hinge.

One alternative configuration for the support member is shown in FIG. 9. Alternative support member (350) comprises a support portion (352), a grommet portion (360), and a living hinge (354) coupling grommet portion (360) to support portion (352). Grommet portion (360) comprises an inner lip (362), an outer lip portion (364), a central portion (366), an outer surface (368), and an inner surface (370). Outer lip portion (364) is substantially similar to outer lip (170) of FIGS. 5-6 or outer lip (210) of FIG. 7 except that outer lip portion (364) is coupled to living hinge (354). Outer lip portion (364) may be integrally formed with living hinge (354) (such as by forming support member (350) as a unitary piece), or outer lip portion (364) may be mechanically or chemically coupled to a portion of living hinge (354) (for instance, if grommet portion (360) is formed separately from support portion (352) and living hinge (354)). Inner lip (362) and central portion (366) may be configured in accordance with at least some of the teachings for inner lip (160) and central portion (152) of FIGS. 5-6 or inner lip (210) and central portion (202) of FIG. 7.

Figure 10:
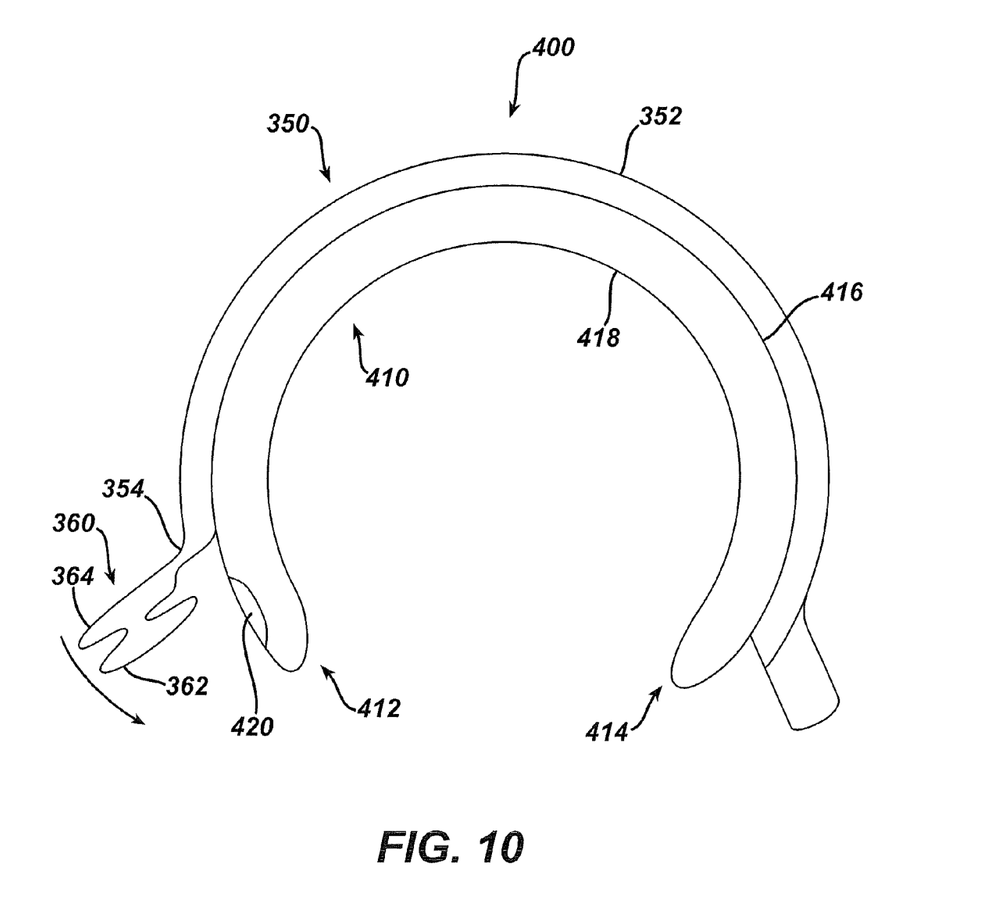
FIG. 10 depicts a side elevation view of the grommet and support member of FIG. 9 overmolded onto a bladder.

FIG. 10 illustrates an alternative gastric band (400) utilizing alternative support member (350) of FIG. 9 with a bladder (410). Gastric band (400) further comprises a strap (not shown) that has been omitted from FIG. 10 to better show alternative support member (350) and bladder (410). Bladder (410) of the present example comprises a first end (412), a second end (414), an outer surface (416), an inner surface (418), an opening (420), and, optionally, a channel (not shown). Bladder (410) may be further configured in substantially the same manner as bladders (100, 310) of FIGS. 5-8. In the present configuration, bladder (410) may initially be formed via injection molding as described above. Bladder (410) is initially removed from the mold, but the core (not shown) still remains within bladder (410). Accordingly, bladder (410) is a curved bladder with the core in the interior of bladder (410) and a portion of the core protruding from opening (420). As shown in FIG. 10, support portion (352) is then overmolded onto outer surface (416) of bladder (410). A reinforcing band (not shown) may be included within the channel of bladder (410) or, in one alternative, overmolded on support member (350). Once support member (350) has coupled to bladder (410), the core within bladder (410) is removed. Living hinge (354) permits grommet portion (360) to rotate such that inner lip (362) is insertable into opening (420). Inner lip (362) and outer lip portion (364) are configured to form an interference fit with the material surrounding opening (420) when inner lip (362) is inserted into opening (420). Such an interference fit may be formed in a substantially similar manner to those described above in relation to grommet (150) of FIGS. 5-6. An adhesive may also be applied to grommet portion (360) to further ensure a fluid-tight seal. Once grommet portion (360) has been inserted into opening (420) to seal bladder (410), the strap may be overmolded on top of support member (350) to form gastric band (400).

In one merely exemplary alternative, support member (350) may initially be formed with a curvature as shown in FIG. 10. In this instance, bladder (410) may then be overmolded onto the inner surface of support portion (352), thereby coupling a portion of outer surface (416) to the inner surface of support portion (352) of support member (350). Gastric band (400) may then be formed in accordance with the previous teachings.

As with gastric band (300) of FIG. 8, support member (350), the strap, and, optionally, the reinforcing band of gastric band (400) substantially constrain outer surface (416) of bladder (410). When fluid is injected into bladder (410) and bladder (410) swells about stomach (2) shown in FIG. 2, the restraint provided by support member (350), the strap, and/or the reinforcing band may urge bladder (410) to compress stomach (2) as opposed to expanding support member (350), the strap, and/or the reinforcing band. Other suitable configurations and features for support member (350), grommet portion (360), and bladder (410) will be apparent to those of ordinary skill in the art in view of the teachings herein.

C. Exemplary Plugs For Bladder

In one alternative, it may be useful to use a plug instead of a grommet to seal an opening formed in bladder (22) by a core used during a process of molding bladder (22). Such a configuration may be useful where the outer surface of bladder (22) may need to be a smooth, continuous surface.

Figure 11:
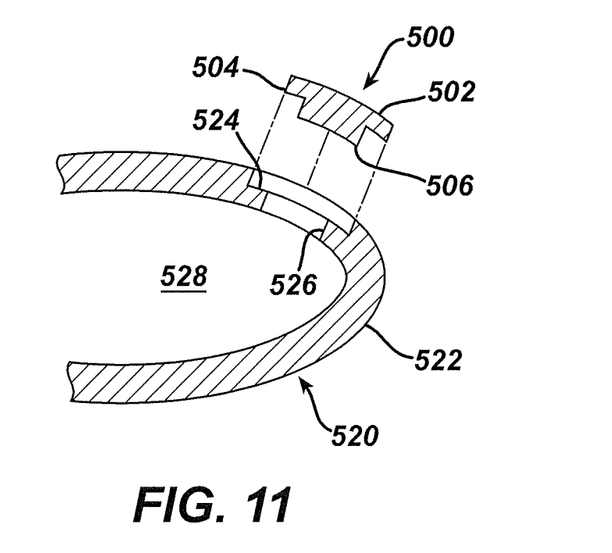
FIG. 11 depicts a partial side cross-sectional view of an exemplary plug for a bladder.

FIG. 11 shows one such exemplary plug (500) for insertion into a bladder (520). In the present example, plug (500) comprises an outer surface (502), a flanged portion (504), and a plug portion (506). Bladder (520) of the present example comprises a body (522) defining an interior (528) of bladder (520). A portion of body (522) of bladder (520) has a shoulder (524) and a complementary plug portion (526). In the present example, bladder (520) is formed via injection molding. Such molding requires a mold and a core to define a cavity into which the material for bladder (520) is injected. In the present configuration, the core and mold have a curvature to form a substantially curved bladder (520) similar to bladder (310), as shown in FIG. 8. In order to remove the core from the newly formed bladder (520), a portion of the core may protrude from the mold. In one merely exemplary configuration, the core and mold may be configured to form shoulder (524) and complementary plug portion (526) as bladder (520) is formed via injection molding. Alternatively, an opening in bladder (520) may be modified by removing material to form shoulder (524) and complementary plug portion (526). By way of example only, portions of opening (110) of bladder (100), as shown in FIG. 5, may be removed to form shoulder (524) and complementary plug portion (526), thereby forming bladder (520). Shoulder (524) and complementary plug portion (526) may be ovular, circular, rectangular, square, triangular, irregularly shaped, or any other suitable shape. In one alternative, complementary plug portion (526) may be sized smaller than plug portion (506) of plug (500) such that complementary plug portion (526) forms an interference fit with plug portion (506) when plug (500) is inserted. Still further configurations for bladder (520) will be apparent to one of ordinary skill in the art in view of the teachings herein.

Plug (500) of the present example may be formed by injection molding to form plug (500) having outer surface (502), flanged portion (504), and plug portion (506). Plug (500) may be a thermoplastic component, a silicone component, a rubber component, or any made from any other suitable material as will be apparent to one of ordinary skill in the art in view of the teachings herein. Plug (500) is shaped to complement to the shape of shoulder (524) and complementary plug portion (526) of bladder (520). Once plug (500) and bladder (520) are formed, plug (500) is inserted into the shoulder (524) and complementary plug portion (526), thereby sealing interior (528) of bladder (520). As noted above regarding grommets (150, 200), an adhesive may be applied to plug (500) to further secure plug (500) to bladder (520). In yet a further configuration, plug portion (506) and/or flange portion (504) may comprise wiper seal type protrusions to engage a surface of complementary plug portion (506) and/or shoulder (524). Such wiper seal protrusions may have triangular cross-sections or semi-circular cross-sections.

With plug (500) inserted into bladder (520), a strap, such as strap (24) of FIG. 1, is overmolded onto bladder (520) to form an assembled gastric band. The strap may be positioned to cover all or part of plug (500), thereby further securing plug (500) to bladder (520). A support member, such as backbone (330), and/or a reinforcement band may be included in the assembled gastric band in accordance with at least some of the previous teachings. The support member and/or reinforcement band may also cover all or part of plug (500) in a similar fashion to the strap. In another variation, support member (350) may be modified to replace grommet portion (360) with plug (500) that is coupled (mechanically, chemically, integrally, and/or etc.) to living hinge (354).

Figure 12:
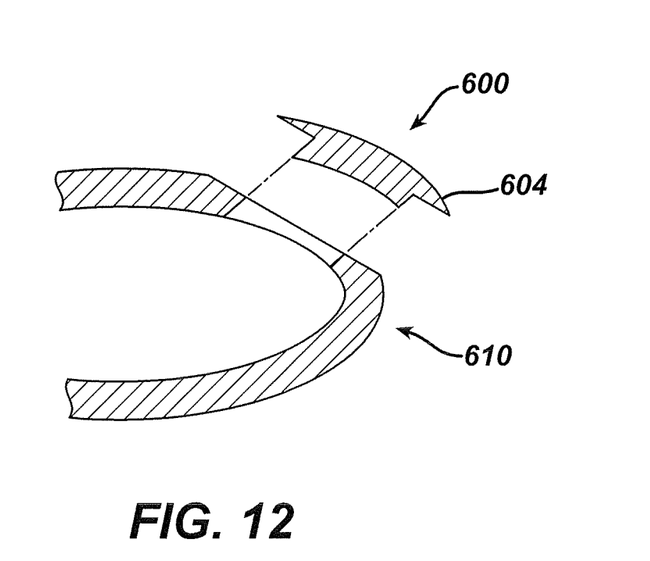
FIG. 12 depicts a partial side cross-sectional view of an exemplary alternative plug for a bladder.

Still further configurations for plug (500) will be apparent to one of ordinary skill in the art in view of the teachings herein. For instance, one alternate configuration for a plug (600) is shown in FIG. 12. Plug (600) comprises a tapered flange portion (604) instead of the squared flange (504) of plug (500). Plug (600) and a complementary bladder (610) may be used to construct a gastric band in a substantially similar manner to the previous discussion regarding plug (500) and bladder (520).

D. Exemplary Gastric Band with Grommet and Integrated Suture Loop

In some instances it may be useful to provide a suture loop on a portion of gastric band (20) to aid in positioning and attaching gastric band (20) during surgery. For instance, a medical instrument having a notch or hook may engage the suture loop to pull the ends of the strap of gastric band (20) together. One merely exemplary medical instrument is disclosed in U.S. Pat. Pub. No. 2011/0144420, entitled "Apparatus for Completing Implantation of Gastric Band," published Jun. 16, 2011, the disclosure of which is incorporated by reference herein. In another situation, an extender may be used with suture loop to initially secure gastric band about the patient's stomach prior to engaging the ends of the strap. Still further, the extender may need to be used with patients who may have large stomachs. Further still, an exposed suture portion disposed between the extender and an end of the strap may permit a surgeon to detach the extender by cutting through the suture portion.

Figure 13:
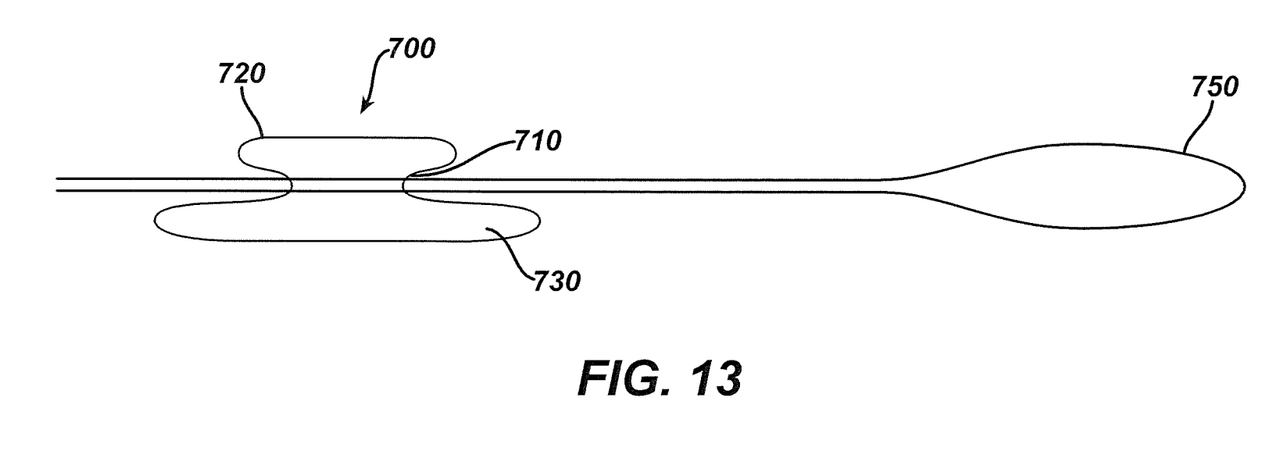
FIG. 13 depicts a side cross-sectional view of an exemplary suture anchored within a grommet.

FIG. 13 depicts an alternative grommet (700) with an integrated suture loop (750).

Grommet (700) of the present example is configured in a substantially similar manner to grommet (150) of FIGS. 5-6, though it should be understood that grommet (700) may be configured in accordance with grommet (200) of FIG. 7, grommet (320) of FIG. 8, grommet portion (360) of FIG. 9-10, plug (500) of FIG. 11, plug (600) of FIG. 12, or any other suitable configuration as will be apparent to one of ordinary skill in the art in view of the teachings herein. In the present configuration, suture loop (750) is inserted into the mold for grommet (700) prior to injecting the material for grommet (700). Accordingly, when grommet (700) is formed, suture loop (750) extends through a central portion (710) of grommet (700). Of course suture loop (750) may alternatively be positioned within an outer lip (720) or inner lip (730) of grommet (700). Still other configurations for grommet (700) and suture loop (750) will be apparent to one of ordinary skill in the art in view of the teachings herein. It should also be understood that suture loop (750) may be otherwise secured to one or more portions of band (760), such that suture loop (750) need not necessarily be molded in grommet (700) or otherwise be secured to grommet (700).

Figure 14:
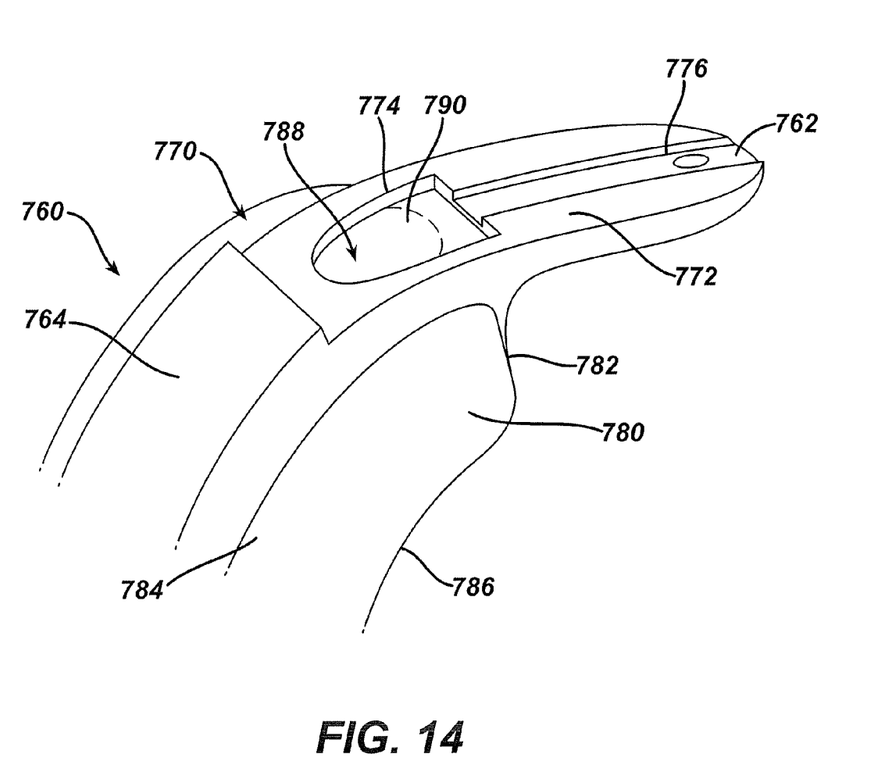
FIG. 14 depicts a partial perspective view of an exemplary bladder and band configured to receive the suture and grommet of FIG. 13.

FIG. 14 depicts an exemplary first end (762) of a band (760) coupled to a bladder (780). Bladder (780) comprises a first end (782), a second end (not shown), an outer surface (784), an inner surface (786), and, optionally, a channel (not shown). First end (782), second end, outer surface (784), and inner surface (786) collectively define an interior (788) of bladder (780). First end (782) comprises an opening (790) configured to receive grommet (700). Bladder (780) may be further configured in accordance with at least some of the teachings of bladders (100, 310, 410, 520, 610) discussed herein.

Band (760) extends along outer surface (784) of bladder (780) or, if a channel is provided, band (760) may be partially or completely disposed within the channel of bladder (780). Band (760) of the present example is a thermoplastic overmolded piece coupled to bladder (780). Band (760) comprises a first end (762) and a main portion (764). First end (762) of the present example comprises a notched region (770) having a deck (772). Notched region (770) further comprises a grommet aperture (774) formed through deck (772) and a suture trough (776) formed in deck (772). It should be understood that suture trough (776) is merely optional. Grommet aperture (774) is configured to substantially align with opening (790) of bladder (780) when band (760) is overmolded onto bladder (780) and is sized to permit at least a portion of grommet (700), such as inner lip (730), to pass through grommet aperture (774). Suture trough (776) extends distally away from grommet aperture (774) to the distal-most end of first end (762). Still other configurations for band (760) and bladder (780) will be apparent to one of ordinary skill in the art in view of the teachings herein.

A portion of grommet (700), such as inner lip (730), is insertable through grommet aperture (774) and into opening (790) of bladder (780). Grommet (700) of the present example couples to opening (790) in a substantially similar manner to grommet (150) and opening (110) of FIGS. 5-6. Suture loop (750) is then positioned within suture trough (776), though if suture trough (776) is not formed within deck (772), suture loop (750) may simply rest atop deck (772). An additional component (not shown) is then overmolded onto notched region (770), thereby securing grommet (700) and a portion of suture loop (750) between the additional component and band (760). In one exemplary configuration shown in FIG. 15, an overmolded finger grip (800) and an overmolded shell (810) are overmolded onto notch region (770) to secure grommet (700) and a portion of suture loop (750). Overmolded finger grip (800) of the present example comprises ridged portions (802) to aid the grip of a user. Overmolded shell (810) comprises a latching member (812) to latch together a first end and a second end of a completed gastric band. Both overmolded finger grip (800) and overmolded shell (810) may be constructed in accordance with at least some of the teachings of U.S. Pat. No. 7,367,937, entitled "Gastric Band," issued May 6, 2008, the disclosure of which is incorporated by reference herein. Still other suitable configurations for overmolded finger grip (800) and overmolded shell (810) will be apparent to one of ordinary skill in the art in view of the teachings herein. For instance, finger grip (800) and overmolded shell (810) may be adhesively secured, mechanically secured (such as by screws, bolts, interference fittings, straps, snaps, rotatable locking members, clips, and/or etc.), and/or in any other suitable securing methods as will be apparent to one of ordinary skill in the art in view of the teachings herein.

Figure 15:
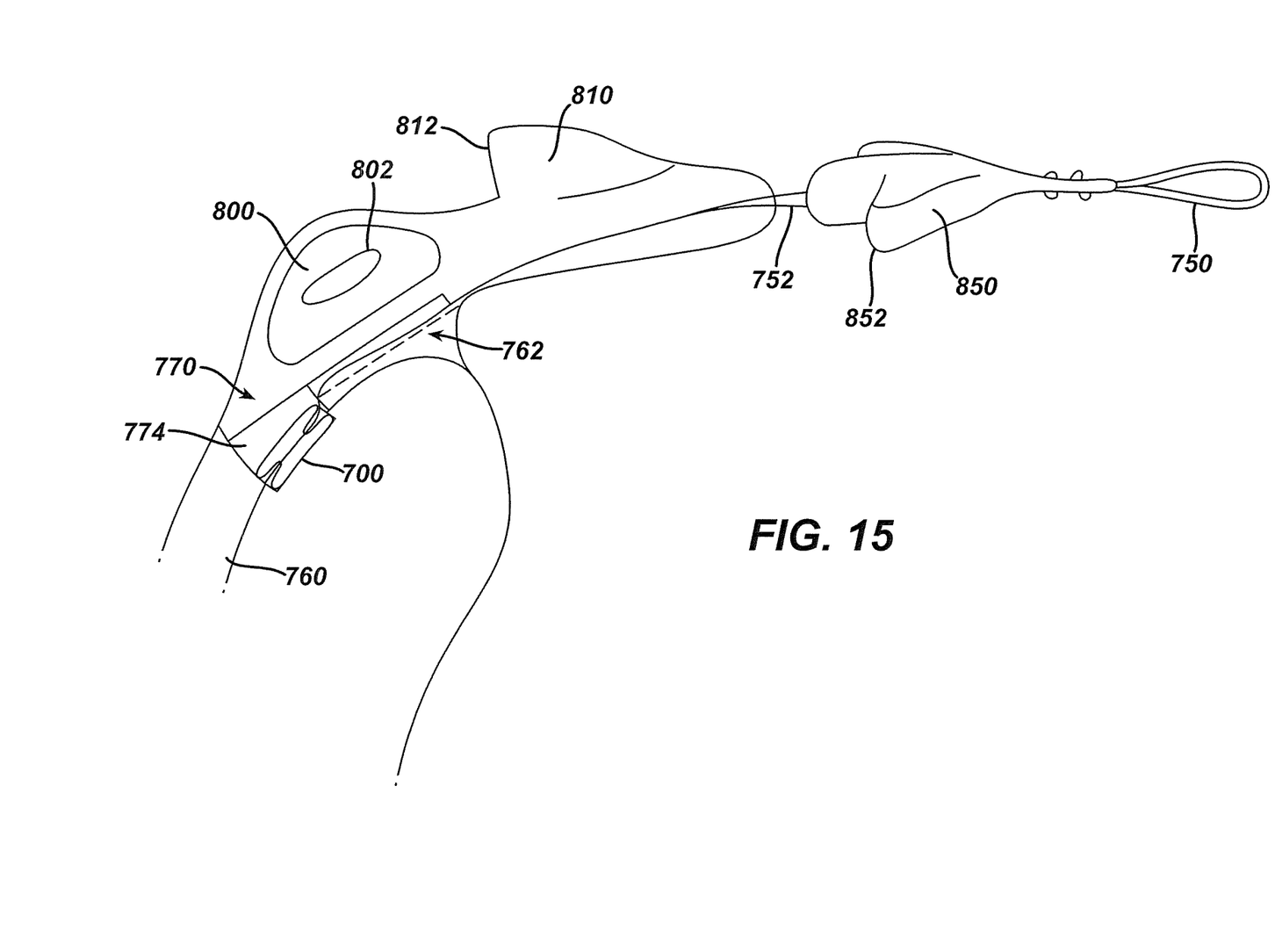
FIG. 15 depicts a partial side elevation view of an exemplary assembly for a gastric band utilizing the suture and grommet of FIG. 13 with the bladder and band of FIG. 14.

An extender (850) is also shown overmolded over a portion of suture loop (750).

The overmolding of extender (850) may be done simultaneously with overmolded finger grip (800) and overmolded shell (810), or extender (850) may be overmolded at a different time (earlier or later). A suture portion (752) separates extender (850) from overmolded shell (810). Suture portion (752) may be cut to detach and remove extender (850) once gastric band (22) is installed. Extender (850) of the present example comprises a wing portion (852) configured to engage a portion of band (760) on the second end of the gastric band. Extender (850) may be further configured in accordance with at least some of the teachings of U.S. Pat. No. 7,367,937, entitled "Gastric Band," issued May 6, 2008. Still other suitable configurations for extender (850) will be apparent to one of ordinary skill in the art in view of the teachings herein.

While some portions of the disclosure include sequentially overmolded components, it should be understood that in some configurations the components may be co-molded or created using a multi-shot molding process.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) a bladder comprising:
        i. a bladder body having an outer surface, and
        ii. an opening formed in the bladder body;
    (b) an insertable component operable to fluidly seal the opening in the bladder body, wherein the insertable component comprises a plug and a suture loop at least partially disposed within the plug; and
    (c) a band having a main portion and a first end, the first end having a notched region comprising:
        i. a deck,
        ii. a plug aperture extending through the deck, and
        iii. a suture trough;
    wherein the band is overmolded onto the outer surface of the bladder body and onto a portion of the insertable component, and
    wherein the opening of the bladder is in substantial alignment with the plug aperture of the band, and wherein the plug is configured to pass completely through the plug aperture and partially into the opening of the bladder.

2. The apparatus of claim 1 comprising an overmolded shell having a latching member, wherein the overmolded shell is overmolded onto the deck to secure the plug and a portion of the suture loop therein.

3. The apparatus of claim 1 wherein the band further comprises a suture loop coupled to the first end of the band.

4. An apparatus comprising:
    (a) a bladder comprising:
        i. a bladder body having an outer surface, and
        ii. an opening formed in the bladder body;
    (b) an insertable component operable to fluidly seal the opening in the bladder body, wherein the insertable component comprises a suture loop; and
    (c) a strap comprising:
        i. a latching member,
        ii. a band, wherein the band presents a suture trough, and wherein the suture loop is disposed within the suture trough, and
        iii. a finger grip having ridged portions, wherein the finger grip is overmolded onto a surface of the band, and wherein the finger grip is configured to secure the suture loop within the suture trough;
    wherein the band of the strap is coupled to the outer surface of the bladder body and a portion of the insertable component.

* * * * *